(12) United States Patent
Knott et al.

(10) Patent No.: US 6,514,713 B1
(45) Date of Patent: Feb. 4, 2003

(54) METHODS OF DETECTING BRCA1 MUTATIONS

(75) Inventors: Christine L. Knott, San Diego, CA (US); Kristine Kuus-Reichel, San Diego, CA (US)

(73) Assignee: Hybritech Incorporated, San Diego, CA (US)

( * ) Notice: Subject to any disclaimer, the term of this patent is extended or adjusted under 35 U.S.C. 154(b) by 0 days.

(21) Appl. No.: 09/898,698

(22) Filed: Jul. 3, 2001

(51) Int. Cl.$^7$ .................. G01N 33/574; G01N 33/53; C07K 16/00; C12P 21/08
(52) U.S. Cl. ............... 435/7.23; 435/7.1; 530/387.7; 530/388.8
(58) Field of Search ............... 435/7.1, 7.23; 530/388.8, 387.7

(56) References Cited

PUBLICATIONS

Taylor, et al., 1998, Int J Cancer, 79:334–342.*
Kashima, et al., 2000, 91(4):399–409.*
Coligan, et al., Current Protocols in Immunology, 2.1.9–2.1.12.*
Futreal et al., BRCA 1 Mutations in Primary Breast and Ovarian Carcinomas, Science, 266: 120–122 (1994).*
Castilla et al., Nature Genet . ., 8:387–391, (1994).*
Plummer, Detection of BRCA 1 Mutations by the Protein Truncation Test, Human Molecular Genetics, 4: 1989–1991 (!995).*
Gao et al., Distal Protein Sequences Can Affect the Function of a Nuclear Localization Signal, Mol. Cell. Biol., 12: 1330–1339, (1992).*
Dawson, Clinical Trials: Analysis and Presentation, Presented at the 26$^{th}$ Annual Meeting of the Association of Medical Diagnostics Manufactures, Available at http://www.amdm.org/AMDM/Newsletter V12–2–2.html, (1999).*
Linnet, Necessary Sample Size for Method Comparison Studies Based on Regression Analysis, Clin. Chem., 45: 882–94, (1999).
Linnet, Evaluation of Regression Procedures for Methods Comparison Studies, Clin. Chem., 45: 882–94, (1993).
Bland et al., Statistical Methods for Assessing Agreement Between Two Methods of Clinical Measurement, Lancet, I: 307–10, (1986).
Reid et al., Use of Methodologic Standards in Diagnostic Test Research, Getting Better But Still not Good, JAMA, 274: 645–51, (1995).
Krouwer, Cumulative Distribution Analysis Graphs–An Alternative to ROC Curves[Tech Brief], Cln. Chem., 33: 2305–6, (1987).
Albert, On The Use and Computation of Likelihood Ratios in Clinical Chemistry, Clin. Chem., 28:1113–9, (1982).
Solberg, Discrimination Analysis, Crit. Rev. Clin. Lab. Sci., 9: 209–42, (1978).
Matthews et al., Analysis of Serial Measurements in Medical Research, Br. Med. J., 300: 230–5, (1990).
Kohler et al., Continuous Cultures of Fused Cells Secreting Antibody of Predefined Specificity, Nature, 256: 495–497, (1975).
Kuus–Reichel et al., Development of Antibodies for Diagnostic Assays, C. P. Price and D. J. Newman (eds.), Principles and Practice of Immunoassay, pp. 37–64, New York: Stockton Press, (1997).

* cited by examiner

*Primary Examiner*—Anthony C. Caputa
*Assistant Examiner*—Natalie A. Davis
(74) *Attorney, Agent, or Firm*—Hogan & Hartson, LLP; William H. May; D. David Hill

(57) ABSTRACT

Methods for detecting BRCA1 mutations are provided. The methods include the steps of determining the amount of the BRCA1 polypeptide contained in a sample of the subject, and correlating the amount of BRCA1 to the presence of the BRCA1 gene mutation in the subject, wherein the amount below a predetermined cutoff value is an indication of the presence of the mutation in the BRCA1 gene of the subject. The methods of the present invention are well suited for use to determine a condition associated with BRCA1 mutation, such as a predisposition to breast cancer, ovarian cancer, colorectal, and prostate cancers, and the presence or prognosis of breast cancer, ovarian cancer, colorectal, and prostate cancers.

14 Claims, 1 Drawing Sheet

METHODS OF DETECTING BRCA1 MUTATIONS

BACKGROUND OF THE INVENTION

1. Area of the Art

The invention relates generally to BRCA1 detection, and specifically to methods of detecting BRCA1 mutations.

2. Description of the Prior Art

Throughout this application, various references are referred to within parentheses. Disclosures of these publications in their entireties are hereby incorporated by reference into this application to more fully describe the state of the art to which this invention pertains. Full bibliographic citation for these references may be found at the end of this application, preceding the claims.

Breast cancer is one of the most commonly diagnosed diseases that affect women. Five to ten percent of breast cancer is associated with inherited factors. Early detection of breast cancer is critical in the medical management of the disease, since treatment of breast cancer at later stages is often futile and disfiguring. Ovarian cancer, although less frequent than breast cancer, is often rapidly fatal and is the fourth most common cause of cancer mortality in American women. Approximately fifty percent of familial breast cancer and eighty percent of familial breast plus ovarian cancer are associated with mutations in the BRCA1 gene located on human chromosome 17q21.3. (1, 2).

BRCA1 appears to be a classical tumor suppressor gene, as BRCA1 protein inhibits the growth of breast and ovarian cancer cell lines and reduces the tumorigenicity of MCF-7 cells. BRCA1 is mutated in some hereditary breast and ovarian cancer. It has been discovered that individuals with the wild-type BRCA1 gene do not have cancer that results from the BRCA1 allele. However, mutations that interfere with the function of the BRCA1 protein are involved in the pathogenesis of cancer. Thus, the presence of an altered (or a mutant) BRCA1 gene which produces a protein having a loss of function, or altered function, directly correlates to an increased risk of cancer.

It has been observed that mutations in the BRCA1 locus in the germline are indicative of a predisposition to breast cancer and ovarian cancer. In addition, somatic mutations in the BRCA1 locus are also associated with breast cancer, ovarian cancer and other cancers, which represent an indicator of these cancers or of the prognosis of these cancers.

The mutational events of the BRCA1 locus can involve deletions, insertions, and point mutations within the coding sequence and the non-coding sequence. Deletions may be the entire gene or only a portion of the gene. Point mutations may result in stop codons, frameshift mutations, or amino acid substitutions. Somatic mutations are those which occur only in certain tissues, e.g., in the tumor tissue, and are not inherited in the germline. Germline mutations can be found in any of a body's tissues or cells and are inherited. If only a single allele is mutated, a predisposition to breast cancer is indicated.

It is believed that BRCA1 predisposing alleles are recessive to wild-type alleles; that is, cells that contain at least one wild-type BRCA1 allele are not cancerous. However, cells that contain one wild-type BRCA1 allele and one predisposing allele may occasionally suffer the loss of the wild-type allele, either by random mutation or by chromosome loss during cell division. All the progeny of such a mutant cell lack the wild-type function of BRCA1 and may develop into tumors. Thus, the predisposing alleles of BRCA1 are susceptible to cancer, and the susceptibility is inherited in a dominant fashion.

Therefore, the finding of BRCA1 mutations provides both diagnostic and prognostic information. It is believed that many mutations found in tumor tissues will be those leading to the decreased expression of the BRCA1 gene product. However, mutations leading to non-functional gene products would also lead to a cancerous state. The majority of mutant alleles are nonsense (10%) or frameshift (71%) and should produce truncated proteins which are predicted to vary in length from 5% to 99% of the full-length protein. Forty-nine percent of these mutations reside in exon 11 which comprises 61% of the BRCA1 coding region. The full-length BRCA1 cDNA sequence and the coding regions of BRCA1 gene have been described in U.S. Pat. No. 5,747,282 (the '282 patent), the content of which is incorporated herein by reference.

So far, the assessment of the status of BRCA1 protein in patients has been limited. The testing of mutations in BRCA1 has been primarily focused on genomic sequencing. One system described is the truncation assay system (3). This system relies on PCR to amplify BRCA1 segments from the genomic DNA of patients. These segments are then transcribed and translated in vitro and the protein generated is analyzed by gel electrophoresis. The appearance of protein bands of a size that is smaller than expected indicates the presence of a mutation in that segment of BRCA1. Clearly, this process is laborious and time-consuming. Also, since so many steps are involved, the chances of getting false results may increase.

More recently, there have been reports of protein-based systems for detecting mutations in the BRCA1 gene (Simple Immunoassays for the Detection of BRCA1 in Cells: *Journal of Clinical Ligand Assay*, Vol. 22, Number 4, 1999 343–347). In this approach, two assays are performed. One measures the presence of full-length protein using one antibody specific for the N-terminal portion of the protein and a second measures the antibody specific for the C-terminal portion of the protein. The second assay uses two antibodies that are both specific for the N-terminal portion of the protein. If a given sample is from an individual who does not have a mutation in the BRCA1 gene, the amount of protein detected by both assays will be comparable. If the sample is from an individual who does have a mutation in the BRCA1 gene and that mutation leads to a truncation of the gene product, then the N-terminal assay measures higher levels of protein present than in the full-length assay. Assays of this type are limited in that they can only detect mutations that result in the generation of truncated protein. Such assays also require the use of two separate measurements which increases the potential for error. A related system is also discussed in U.S. Pat. No. 5,965,377.

Therefore, a need exists for developing a simpler, more effective method for assessing the status of BRCA1 proteins in patients. The finding of BRCA1 mutations provides both diagnostic and prognostic information.

SUMMARY OF THE INVENTION

The present invention is based on the discovery that cells with mutated BRCA1 have lower levels of BRCA1 protein compared to cells with wild-type BRCA1. Therefore, by measuring the level of BRCA1 protein contained in a sample of a subject, one may determine the mutational status of BRCA1 in the subject.

Accordingly, one aspect of the present invention provides a method of detecting and determining the presence of BRCA1 gene mutation in a sample. The method includes the steps of determining the amount of BRCA1 polypeptide contained in the sample, and correlating the amount of BRCA1 polypeptide to the presence of the BRCA1 gene mutation in the sample, wherein the amount below a predetermined cutoff value is an indication of the presence of BRCA1 gene mutation in the sample.

Another aspect of the present invention provides a method for determining the presence of a condition associated with BRCA1 mutation comprising the steps of:

(a) determining the amount of BRCA1 polypeptide contained in a sample of the subject, and (b) correlating the amount of BRCA1 polypeptide to the presence of the condition, wherein the amount below a predetermined cutoff value is an indication of the condition.

In accordance with embodiments of the present invention, the condition associated with BRCA1 mutation includes, but is not limited to, a predisposition to breast cancer or ovarian cancer, and the presence or prognosis of breast cancer or ovarian cancer.

The methods of the present invention are well suited for use to provide both diagnostic and prognostic information on diseases associated with mutations of BRCA1. The methods are also well suited for use in connection with immunoassay, image analysis, flow cytometry, or laser scanning cytometry technologies.

The invention is defined in its fullest scope in the appended claims and is described below in its preferred embodiments.

BRIEF DESCRIPTION OF THE DRAWINGS

The above-mentioned and other features of this invention and the manner of obtaining them will become more apparent, and will be best understood by reference to the following description, taken in conjunction with the accompanying drawings. These drawings depict only a typical embodiment of the invention and do not therefore limit its scope. They serve to add specificity and detail, in which.

DETAILED DESCRIPTION OF THE INVENTION

Figure 1:
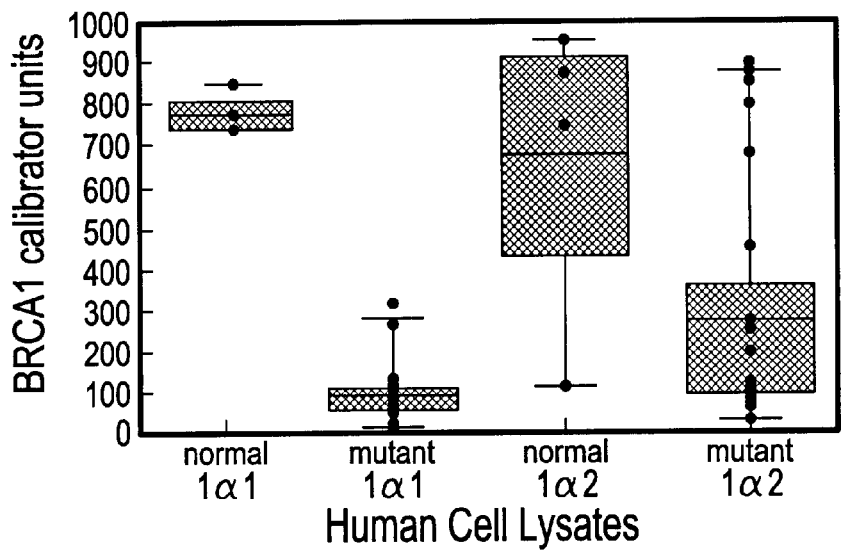
FIG. 1 is a diagram that shows the statistical comparison of Normal and BRCA1 mutant HLC in the N-terminal assay.

One aspect of the present invention provides a method for detecting and determining the presence of a mutation in BRCA1 gene of a subject. The method includes the steps of (a) determining the amount of BRCA1 polypeptide contained in a sample of the subject, and (b) correlating the amount of BRCA1 polypeptide to the presence of a mutation in BRCA1 gene of the subject, wherein the amount below a predetermined cutoff value is an indication of the presence of a mutation in BRCA1 gene of the subject.

"BRCA1 protein or BRCA1 polypeptide" refers to a protein or a polypeptide encoded by the BRCA1 locus, variants, or fragments thereof. The term "polypeptide" refers to a polymer of amino acids and its equivalent and does not refer to a specific length of the product; thus, peptides, oligopeptides, and proteins are included within the definition of a polypeptide. For example, the BRCA1 polypeptide may include a full-length polypeptide of BRCA1, a portion of the full-length, a truncated polypeptide, a polypeptide that contains only the truncated portion, and the mutated polypeptide. This term also includes modifications of the polypeptide as long as the modified polypeptide retains the immunological activities. Examples of the modification include, but are not limited to, deletion, truncation, glycosylations, acetylations, phosphorylations, and the like. In addition, polypeptides that contain one or more analogs of an amino acid (including, for example, natural amino acids, etc.) and polypeptides with substituted linkages, as well as other modifications known in the art, both naturally or non-naturally occurring, are also contemplated.

For the purpose of the present invention, the terms "BRCA1 locus, BRCA1 gene, or BRCA1 polynucleotide" are used interchangeably; each refers to polynucleotides, all of which are in the BRCA1 region that are likely to be expressed in normal tissue, certain alleles of which predispose an individual to develop breast, ovarian, colorectal, and prostate cancers. Mutations at the BRCA1 locus or gene may be involved in the initiation and/or progression of other types of tumors. The locus is indicated in part by mutations that predispose individuals to develop cancer. These mutations fall within the BRCA1 region described. The BRCA1 locus or gene is intended to include coding sequences, intervening sequences, and regulatory elements controlling transcription and/or translation. The BRCA1 locus or gene is intended to include all allelic variations of the DNA sequence.

These terms, when applied to a nucleic acid, refer to a nucleic acid which encodes a BRCA1 polypeptide, fragment, homolog or variant, including, e.g., protein fusions or deletions. The nucleic acids of the present invention will possess a sequence that is either derived from, or substantially similar to, a natural BRCA1-encoding gene or one having substantial homology with a natural BRCA1-encoding gene or a portion thereof. The coding sequence for a BRCA1 polypeptide is shown in SEQ ID NO:1 of U.S. Pat. No. 5,747,282 (the '282 patent), with the amino acid sequence shown in SEQ ID NO:2 of the '282 patent, and the contents of which are incorporated herein by reference in its entirety.

The term "germline mutation", as used herein, indicates a deleterious alteration in one BRCA1 allele which is present in every nucleous containing cell of the body. When the second BRCA1 allele of an individual cell becomes damaged or mutated, that cell and all its progeny are predisposed to become cancerous. This is distinct from normal polymorphisms, non-deleterious alterations in the nucleotide sequence that do not predispose the individual to cancer. The term "somatic mutation" refers to a deleterious alteration in at least one BRCA1 allele that is not found in every cell of the body, but is found only in isolated cells. Typically, these cells will be those that make up a breast tumor. The mutations in the BRCA1 gene include any alteration of nucleic acids of BRCA1 polynucleotides, such as, but not limited to, an insertion, deletion, frameshift, or base substitution. For example, a mutated BRCA1 gene may contain a full-length BRCA1 polynucleotide with base substitutions; a portion of the full length; a truncated BRCA1 polynucleotide, i.e., the one with a deletion of most of exon 11; or the deleted portion of the BRCA1 polynucleotide, such as the exon 11.

For the purpose of the present invention, the amount of the BRCA1 polypeptide contained in a sample may be determined by any methods that are described herein, or known in the art or developed later, as long as they are capable of making such a determination. For example, one may use any in vitro assay of any form, a binding assay, or a cell counting/sorting method that exploits the specific binding of an antibody to BRCA1 for the purpose of the present invention to measure the amount of BRCA1 polypeptide in a fluid sample. The general methods of the in vitro detection of antigenic substances in patient fluid samples or tissue sample by immunoassay or immunohistochemical procedures are also well known in the art and require no repetition herein.

In accordance with one embodiment of the present invention, a BRCA1 polypeptide contained in a sample may be measured by a method including the steps of contacting an antibody that recognizes and binds to the BRCA1 protein with the sample under a condition that allows the formation of a complex comprising the antibody and the BRCA1 protein, and detecting and determining the amount of the complex.

For the purpose of the present invention, the term "antibody" includes monoclonal and polyclonal antibodies. Methods of making antibodies that recognize and bind to BRCA1 polypeptides are described in the commonly owned co-pending U.S. application Ser. No. 09/136,863, the contents of which are incorporated herein in its entirety by reference. Briefly, antibodies are made from the immunization of animals with an antigen containing human BRCA1 proteins, i.e., the recombinant BRCA1 described in the co-pending patent application Ser. No. 09/136,863, or fragments thereof, by methods well-known in the art. For polyclonal antibodies, anti-serum containing the antibodies is collected from the immunized animals. For monoclonal antibodies, spleen cells from the immunized animals are fused with an appropriate immortalized cell line (e.g., a myeloma cell line from the same animal species) under conditions that produce an immortalized antibody-producing fused cell line. Clones of cells producing the antibody of interest can be selected by assaying cell supernatants for reactivity with the antigen. For production of monoclonal antibodies, fused cells can be grown either in vitro in mass culture or in vivo in a histocompatible animal species. Monoclonal antibodies offer advantages over polyclonal antibodies, as they are of a single immunologic species (i.e., they recognize a single epitope on the antigen molecule) and can be produced on an ongoing basis from the immortalized cell line.

If desired, both polyclonal antibodies or monoclonal antibodies can be used. Polyclonal antibodies can be purified from crude anti-serum by, for example, binding and elution from a matrix to which is bound a polypeptide or peptide to which the antibodies were raised. Those skilled in the art will know of various techniques common in the immunology arts for purification and/or the concentration of polyclonal, as well as monoclonal, antibodies.

The term "antibody," as used in this invention, includes intact molecules as well as fragments thereof, such as Fab, Fab', F(ab')$_2$, Fv, and SCA, which are capable of binding the epitopic determinant. These antibody fragments retain the ability to selectively bind with the relative antigen and are defined as follows:

1. Fab: the antibody fragment that contains a monovalent antigen-binding fragment of an antibody molecule; this fragment can be produced by, for example, digestion of the whole antibody with the enzyme papain to yield an intact light chain and a portion of one heavy chain; the Fab fragment lacks the Fc region;
2. Fab': the antibody fragment that can be obtained by, for example, treating the whole antibody with pepsin, followed by reduction, to yield an intact light chain and a portion of the heavy chain; the Fab' fragment contains a portion of the Fc region;
3. F(ab')$_2$: the fragment of the antibody that can be obtained by, for example, treating the whole antibody with the enzyme pepsin without subsequent reduction; F(ab')$_2$ is a dimer of two Fab' fragments held together by two disulfide bonds and also contains a portion of the Fc region;
4. Fv: defined as a genetically engineered fragment containing the variable region of the light chain and the variable region of the heavy chain expressed as two chains; and
5. Single Chain Antibody ("SCA"): defined as a genetically engineered molecule containing the variable region of the light chain, the variable region of the heavy chain, linked by a suitable polypeptide linker as a genetically fused single chain molecule.

Methods of making these fragments are known in the art (4).

The antibodies that bind BRCA1, whether monoclonal or polyclonal antibodies, can be utilized in a liquid phase or bound to a solid phase.

The antibodies can be bound to many different solid phases and used to determine the amount of BRCA1. Examples of well-known solid phases include glass, polystyrene, polypropylene, polyethylene, dextran, nylon, amylases, natural and modified celluloses, polyacrylamides, agaroses, and magnetites. The nature of the solid phase can be either soluble or insoluble for purposes of the invention. Examples of insoluble solid phases include, but are not limited to, a bead or a microtiter plate. Those skilled in the art will know of other suitable solid phases or will be able to ascertain such under routine experimentation.

In addition, the BRCA1 antibodies of the present invention can be labeled in various ways. For example, the agent(s) can be coupled to low molecular weight haptens. These haptens can then be specifically detected by means of a second reaction. For example, it is common to use such haptens as biotin, which react with avidin, or dinitrophenyl, pyridoxal, and fluorescein, which can react with specific anti-hapten antibodies. The BRCA1 antibodies of the present invention can also be coupled with a detectable label, such as an enzyme, radioactive isotope, fluorescent compound or metal, chemiluminescent compound, or bioluminescent compound. Furthermore, the binding of these labels to the desired molecule can be done using standard techniques common to those of ordinary skill in the art.

One of the ways in which the BRCA1 antibody can be labeled is by linking it to an enzyme. This enzyme, in turn, when later exposed to its substrate, will react with the substrate in such a manner as to produce a chemical moiety which can be detected by, for example, spectrophotometric or fluorometric means (ELISA system). Examples of enzymes that can be used as detectable labels are horseradish peroxidase, malate dehydrogenase, staphylococcal nuclease, delta-5-steroid isomerase, yeast alcohol dehydrogenase, alpha-glycerophosphate dehydrogenase, triose phosphate isomerase, alkaline phosphatase, asparaginase, glucose oxidase, beta-galactosidase, ribonuclease, urease, catalase, glucose-6-phosphate dehydrogenase, glucoamylase, and acetylcholine esterase.

For increased sensitivity in the ELISA system, the procedures described can be modified using biotinylated antibodies reacting with avidin-peroxidase conjugates.

The amount of BRCA1 complexes can also be determined by labeling the BRCA1 antibodies with a radioactive isotope. The presence of the radioactive isotope would then be determined by such means as the use of a gamma counter or a scintillation counter. Isotopes which are particularly useful are $^{3}$H, $^{125}$I, $^{123}$I, $^{32}$P, $^{35}$S, $^{14}$C, $^{51}$Cr, $^{36}$Cl, $^{57}$CO, $^{58}$CO, $^{59}$Fe, $^{75}$Se, $^{111}$N, $^{99}$Tc, $^{67}$Ga, and $^{90}$Y.

The determination of the BRCA1 concentration of a sample is also possible by labeling the BRCA1 antibody(ies) with a fluorescent compound. When the fluorescent-labeled molecule is exposed to light of the proper wavelength, its presence can then be detected due to the fluorescence of the dye. Among the most important fluorescent-labeling compounds are fluorescein isothiocyanate, rhodamine, phycoerythrin, phycocyanin, allophycocyanin, ophthaldehyde, and fluorescamine.

Fluorescence-emitting metal atoms, such as Eu (europium) and other lanthanides, can also be used. These can be attached to the desired molecule by means of metal-chelating groups, such as DTPA or EDTA.

Another way in which the BRCA1 antibody(ies) can be labeled is by coupling it to a chemiluminescent compound. The presence of the chemiluminescent-tagged immunoglobulin is then determined by detecting the presence of the luminescence that arises during the course of a chemical reaction. Examples of particularly useful chemiluminescent-labeling compounds are luminol, isoluminol, aromatic acridinium ester, imidazole, acridinium salt, and oxalate ester.

Likewise, a bioluminescent compound may also be used as a label. Bioluminescence is a special type of chemiluminescence which is found in biological systems and in which a catalytic protein increases the efficiency of the chemiluminescent reaction. The presence of a bioluminescent molecule would be determined by detecting the presence of luminescence. Important bioluminescent compounds for purposes of labeling are luciferin, luciferase, and aequorin.

Qualitative and/or quantitative determinations of the BRCA1 concentration of a sample may be accomplished by competitive or non-competitive assay procedures in either a direct or indirect format. Examples of such assays are the radioimmunoassay (RIA) and the sandwich immunoassay (or immunometric assay). The measurement of the BRCA1 can be done utilizing assays which are run in either the forward, reverse, or simultaneous modes. Those skilled in the art will know, or can readily discern, other assay formats without undue experimentation.

The term "immunometric assay" or "sandwich immunoassay" includes a simultaneous sandwich, forward sandwich, and reverse sandwich immunoassay. These terms are well understood by those skilled in the art. Those skilled in the art will also appreciate that BRCA1 antibodies according to the present invention will be useful in other variations and forms of assays which are presently known or which may be developed in the future. These are intended to be included within the scope of the present invention. For example, they may be used in connection with well-known immunoassays, such as ELISA, Western Blot, immunoprecipitation, flow cytometry, immunofluorescence, and immunohistology, for detecting a mutation of BRCA1 protein.

For the purpose of the present invention, any equivalents of the above-discussed antibodies may also be used for measuring the amount of BRCA1. For example, any molecular species, known or developed later, capable of recognizing and binding to a BRCA1 polypeptide will be considered as equivalents of the antibodies, and therefore may be used for measuring the amount of BRCA1. Such equivalents of the antibodies may be selected by methods known in the art. For example, any known binding assays may be used to determine the binding activity of any given molecule. Examples of potential molecular species include, but are not limited to, antigen-binding fragments derived from antibodies and aptamers.

In accordance with one embodiment of the present invention, monoclonal antibodies that recognize and bind to a BRCA1 polypeptide are used. Monoclonal antibodies recognize and bind to a BRCA1 polypeptide if they can recognize an epitope of a human BRCA1 polypeptide and bind to the epitope. As used herein, "epitope" refers to an antigenic determinant of a polypeptide. An epitope can comprise three amino acids in a spatial conformation which is unique to the epitope. Generally, an epitope consists of at least five such amino acids, and usually consists of at least 8–10 such amino acids. Methods of determining the spatial conformation of such amino acids are known in the art.

Monoclonal antibodies that recognize and bind to a BRCA1 polypeptide, and methods of making those monoclonal antibodies, are described in detail in the commonly owned co-pending U.S. patent application Ser. No. 09/136,863, the relevant content of which is incorporated herein by reference.

In one embodiment of the present invention, monoclonal antibodies are monoclonal antibodies against the N-terminal region of a BRCA1 polypeptide of the present invention. As used herein, the N-terminal region of a BRCA1 polypeptide is a region of the polypeptide having the N-terminal amino acids of a full-length BRCA1 polypeptide, as shown in SEQ ID NO:2 of the '282 patent. Examples of the monoclonal antibodies include, but are not limited to, monoclonal antibodies BR1N129.5 and BR1N411.4 (raised against GST-BRCA1 aa 1–304 fusion protein).

In another embodiment of the present invention, monoclonal antibodies of the present invention are monoclonal antibodies against the C-terminal region of a full-length BRCA1 polypeptide. As used herein, the C-terminal region of a BRCA1 polypeptide is a region of the polypeptide having the C-terminal amino acids of a full-length BRCA1 polypeptide, as shown in SEQ ID NO:2 of the '282 patent. The "end region" of a BRCA1 polypeptide is a region of the polypeptide having either the N-terminal or C-terminal amino acids of a full-length BRCA1 polypeptide. Examples of the monoclonal antibodies include, but are not limited to, monoclonal BR1S218.1, BR1S060.2, BR1S384.5, and BR1S425.1, all of which are immunoreactive with the C-terminal peptide of BRCA1 (aa 1840–1862).

Further, in another embodiment of the present invention, monoclonal antibodies of the present invention are monoclonal antibodies against a portion of a BRCA1 polypeptide between the N-terminal and C-terminal regions of the BRCA1 polypeptide. The term "a portion," as used herein, includes any region of a BRCA1 polypeptide that does not contain both the N-terminal and the C-terminal of a full-length BRCA1 polypeptide. Ln one embodiment of the present invention, the portion may be a region of BRCA1 polypeptide that is often mutated in breast and ovarian cancer patients. For instance, the portion may be a region that is deleted from a truncated BRCA1 polypeptide. An example of the monoclonal antibodies includes, but is not limited to, monoclonal antibodies BR1H788.6, BR1H945.2 AND BR1H826.5, which have a reactivity to a portion of a BRCA1 polypeptide (aa 1360–1555).

Monoclonal antibodies of the present invention may be paired together to be used in an immunometric assay described in the co-pending U.S. patent application Ser. No. 09/136,863 for measuring the amount of BRCA1 polypeptides in a sample. For example, when the BRCA1 polypeptides to be measured are contained in a fluid sample, two monoclonal antibodies may be used. One monoclonal antibody may serve as a capturing antibody which is attached to a solid carrier discussed above for capturing the BRCA1 polypeptides contained in the sample. Preferably, the capturing monoclonal antibody is a monoclonal antibody immunoreactive with a region of the BRCA1 polypeptide that is not mutated, although a monoclonal antibody against a region that is mutated may also be used. In one embodiment of the present invention, a monoclonal antibody against the N-terminal of the BRCA1 protein is used. Monoclonal antibodies against other regions of the BRCA1 may also be used as long as those regions do not contain any mutations to prevent the binding of the monoclonal antibody to the antigenic substance.

The other monoclonal antibody serves as a detecting antibody which is often labeled for easier detection. In theory, the second monoclonal antibody can be any monoclonal antibody against the BRCA1 protein, provided that binding of this monoclonal antibody will not interfere with the binding of the capturing monoclonal antibody to the BRCA1 protein.

Since the method of the present invention relies upon the detection of the formation of an antibody:antigen:antibody sandwich, preferably two different monoclonal antibodies which do not interfere with the binding of each other to the antigen are selected to be the capturing antibody and the detecting antibody. However, the same monoclonal antibody can be used for both the detecting antibody and the capturing antibody when the antigenic substance possesses identical antibody binding sites sufficiently remote from each other to allow more than one antibody molecule to be bound at the same time.

Examples of monoclonal antibodies which may be used in a method of the present invention to detect a mutation in BRCA1 include, but are not limited to, BR1N129.5, BR1H945.2, BR1N411.4, BR1H826.5, BR1H788.6, BR1S060.2, BR1S218.1, BR1S384.5, and BR1S425.1.

For the purpose of the present invention, a condition is sufficient if it allows the binding of an antibody to a BRCA1 polypeptide to form a complex. Examples of the conditions for the formation of the complex are set forth below in the examples. One skilled in the art can readily determine the conditions without undue experimentation in view of the disclosure of the present invention.

For the purpose of the present invention, the sample may be a fluid, a whole cell, or a tissue section. Examples of a fluid include, but are not limited to, peripheral blood lymphocyte (PBL) lysates, tissue lysates, cells lysates, and serum samples. Preferably, the sample is from a mammal, more preferably from a human. If the sample is not a fluid, preferably the sample may be fixed with a chemical reagent. The chemical regent can be any of the reagents commonly used in flow cytometry, in situ hybridization, and immunohistochemistry for the purpose of fixing cells or tissue sections. Examples of the chemical reagents include, but are not limited to, paraformaldehyde, formatin, paraffin, and the like.

For the purpose of the present invention, the amount of the BRCA1 polypeptide detected in a sample of a subject may be correlated to the presence of a mutation in the BRCA1 gene of the subject in any way that generates a useful value for determining the presence of the mutation. It is a discovery of the present invention that the level of the BRCA1 protein is decreased in patients with germline mutations in the BRCA1 gene. Therefore, in accordance with one embodiment of the present invention, by comparing the amount of BRCA1 contained in a sample of a subject to a predetermined cutoff value, one can readily determine the presence of a mutation in the BRCA1 gene of that subject.

In view of the teaching of the present invention, one skilled in the art through routine experimentation can readily determine the "predetermined cutoff value" (or threshold) or other analytical parameters necessary to allow the use of the level of the BRCA1 protein in determining the presence of a condition associated with the BRCA1 gene mutations. For example, one may compare the amount of the BRCA1 protein contained in samples from a series of subjects with the wild-type BRCA1 gene to the amount of the BRCA1 protein contained in samples from a series of subjects known to possess deleterious mutations in the BRCA 1 gene. Those subjects possessing deleterious mutations will frequently be those with a particular condition discussed above. Receiver Operating Characteristic (ROC) analysis can then be used to determine a cutoff value with required specificity and sensitivity. ROC analysis is know in the art and is described in detail in reference 5 (5), the relevant content of which is incorporated herein by reference. Then the amount of BRCA1 of a sample of a subject to be tested may be compared to the predetermined cutoff value for determining the presence of the condition, wherein the amount below the predetermined cutoff value is an indication of the presence of the condition. This and other methods of determining the cutoff value with required specificity and sensitivity are well known in the art and need not be repeated (5–13).

The immunoassay of the present invention is well suited for use in detecting a mutation in BRCA1 contained in a sample from a patient with breast cancers, ovarian cancers, colorectal, and prostate cancers. It is been observed that mutations in the BRCA1 locus in the germline are indicative of a predisposition to breast cancer and ovarian cancer. In addition, somatic mutations in the BRCA1 locus are also associated with breast cancer, ovarian cancer and other cancers, which represent an indicator of these cancers or of the prognosis of these cancers. Therefore, the detection of a mutation may be used to determine the predisposition of a patient or for the diagnosis or prognosis of cancers.

Accordingly, another aspect of the present invention provides a method for determining the presence of a condition associated with the mutation of BRCA1 in a subject. The method comprises the steps of (a) determining the amount of BRCA1 protein contained in a sample of the subject, and (b) correlating the amount of BRCA1 protein to the presence of the condition, wherein the amount below a predetermined cutoff value is an indication of the condition.

For the purpose of the present invention, a condition is associated with a mutation of BRCA1 if the mutation in BRCA1 is a flaw that contributes to the condition. Examples of the condition include, but are not limited to, a predisposition to breast cancer, ovarian cancer, colorectal, and prostate cancers, and the presence or prognosis of breast cancer, ovarian cancer, colorectal, and prostate cancers.

The invention is further described by reference to the following examples.

EXAMPLES

Methods of Detecting BRCA1 Mutations Materials and Methods

Recombinant Expression of Immunogens and Peptide Syntheses

Different fragments of BRCA1 cDNA were amplified by PCR and cloned into *E.coli* expression vectors. PET vectors (Novagen Inc., Madison, Wis.) and the PGEX vectors (Promega, Madison, Wis.) were used to express the recombinant proteins fused to T7 and GST leader sequences, respectively. Plasmids were propagated in *E.coli* BL21 (T7 fusion proteins) or *E.coli* DH5α (GST fusion proteins).

Protein expression was induced with IPTG. Cell pellets were isolated, washed and, if soluble, purified by reverse phase HPLC or, if insoluble, eluted from SDS/PAGE. The identity of the purified proteins was confirmed by N-terminal amino acid sequencing.

Peptides were synthesized using standard F-moc solid phase chemistry on an Applied Biosystems 431A peptide synthesizer. Peptides were purified by HPLC and analyzed by mass spectrometry and analytical HPLC.

Monoclonal Antibody Production

Murine monoclonal antibodies (Mabs) BR1N129.5 and BR1N411.4 were generated against bacterially-expressed fusion proteins containing BRCA1 aa 1–304. BR1H945.2, BR1H826.5, and BR1H788.6 Mabs were generated against bacterially-expressed fusion proteins containing BRCA1 aa 1360–1555. BR1S060.2, BR1S218.1, BR1S425.1 and BR1S384.5 Mabs were generated against a synthetic peptide containing BRCA1 aa 1840–1862. Mabs were affinity purified from ascites using a Protein A/G column.

1. Mice

Female A/J mice were purchased from Jackson Laboratories (Bar Harbor, Me.). Female Balb/c and nude mice were purchased from Harlan Sprague Dawley (Indianapolis, Ind.). All mice were maintained on standard lab chow and tap water, ad libitum.

2. Immunization

Balb/c and A/J mice were immunized with 50 µg of peptide conjugated to KLH or 50 µg of fusion protein, i.p. on day 1, using alum (Sigma, Chicago, Ill.) or Complete Freund's Adjuvant (CFA) (Difco, Detroit, Miss.) as adjuvant. Mice were injected with 25 µg of antigen with adjuvant on day 14. Mice were bled on day 21 for serum titer analysis. Mice with the highest serum titers to the immunogen were selected for fusion.

3. Fusion Procedure

Hybridomas were made using standard techniques (15, 16). Spleen cells were depleted of T cells with anti-Thy 1.2 antibody (Cedarlane Labs, Westbury, N.Y.) and rabbit complement (Cedarlane). T cell depleted spleen cells were fused with P3.653 myeloma cells. Cells were plated at $2 \times 10^5$ spleen cells per well. Supernatant from wells with growing hybridomas were screened by ELISA against the immunogen to determine the presence of antigen specific, antibody producing cells. Selected cell lines were subcloned using a FACStar Plus cell sorter equipped with an automatic cell deposition unit (Becton-Dickinson, San Jose, Calif.).

4. ELISA

BRCA1 aa 1–304 fusion protein was dried down overnight on 96 well microtiter plates (Falcon, Lincoln Park, N.J.) at 1 µg/ml. After washing with distilled water, plates were blocked for 30 minutes with 7% non-fat milk (Carnation, Glendale, Calif.) and washed again. Fifty microliters of sample was added per well and incubated for 1 hour. After washing, 100 µl per well of goat anti-mouse IgG (Fc)-HRP (1:1000, Jackson immunoresearch, West Grove, Pa.) was added for 1 hour. Plates were washed and developed with OPD (o-phenylenediamine dihydrochloride) (Sigma) in 50 mM phosphate-citrate buffer, pH 5.0, quenched with 4N $H_2SO_4$, and read at 490 nm on an ELISA reader (Biotek Instruments, Burlington, Vt.).

BRCA1 fusion protein 1360–1555 and peptide 1840–1862 were biotinylated with an EZ Link biotinylation kit, according to manufacturer's directions (Pierce Chemicals, Rockford, Ill.). Fifty microliters of Mab sample were added to pre-coated strepavidin plates (Wallac Inc, Gaithersburg, Md.) and mixed with 0.1 µg/ml biotinylated antigen for one hour with shaking. After washing with PBS/Tween 20, 100 µl of diluted goat anti-mouse IgG (Fc)-HRP (Jackson Immunoresearch) was added in 10% horse serum (Gibco BRL, Grand Island, N.Y.) for one hour with shaking. After washing, plates were developed as described above.

A more detailed description of the above materials and methods is also provided in the co-pending patent application Ser. No. 09/136,863, the relevant content of which is incorporated herein by reference. In addition, the generation of immunogen, monoclonal antibody production, and antibody characterization have also been described in detail in the *Journal of Clinical Ligand,* "Simple Immunoassays for the detection of BRCA1 in Cells", Volume 22, Number 4, 1999, the relevant content of which is also incorporated herein by reference.

Cell Lines

Human EBV transformed lymphoblastoid cell lines (HLC) were obtained from the Genetics & IVF Institute, Fairfax, Va. and Coriell Cell Repositories, Camden, N.J. Cell lines were maintained in RPMI media (Gibco) with 10% Fetal Clone (Hyclone, Logan, Utah) and 2 mM L-glutamine (Sigma) in a 5% $CO_2$ incubator.

Cell lines identified as having no alterations in the nucleic acid sequence of the BRCA1 gene are considered normal and assumed to produce wild type BRCA1 polypeptide. Cell lines identified as having at least one alteration in the nucleic acid sequence of the BRCA1 gene are considered mutants and assumed to produce altered or truncated BRCA1 polypeptide. A summary of the cell lines and alterations in the nucleic acid sequence is provided in Table 1.

Two "lots" of cell lysate were prepared from each cell line. These "lots" were made on two different days but followed the same procedure for the preparation. Each lot was run in both the N-terminal and full-length assays. Results are shown in Table 2.

Lysate Preparation

HLC lines were seeded at $2 \times 10^5$ cells/ml in culture flasks and grown for 48 hours. Cells were harvested, counted by trypan blue to determine cell concentration and viability, centrifuged, and washed in PBS. Cells were lysed at a concentration of $1 \times 10^6$ cells/10 µl of lysis buffer (10 mM Tris, pH 7.5, 150 mM NaCl, 1% Triton X-100, 5 mM EDTA, 5 mM $NaN_3$, 10 mM sodium phosphate, 10 mM sodium pyrophosphate, and a cocktail of protease inhibitors) (Sigma). After a 30 minute incubation on ice, lysates were centrifuged at 10,000×g for 15 minutes at 4° C. The supernatant was collected and frozen at −70° C. From each cell line, two "lots" of lysates were made on two separate days. The first lysate was designated as "lot 1" and the second as "lot 2".

Fusion Protein Calibrator

A 1.6 kb band coding for amino acids 1–304 and 1313–1555 was amplified and cloned into the pCR2.1 vector (Invitrogen, Carlsbad, Calif.) and used to transform competent DH5α cells (Gibco). The plasmid was purified from these cells and the BRCA1 band digested out using restriction enzymes. The resulting band was cloned into the pET3b vector (Novagen), creating plasmid pBR2J. The epitope for the C-terminal antibodies (aa 1852–1863) was added to this plasmid using similar methods. Most of the BRCA1 insert in the resulting plasmid, pBR2P, was sequenced from both ends. No mutations were seen. Competent BL21(DE3) cells (Novengen) were transformed with plasmid pBR2P. The fusion protein was overexpressed as detected by SDS-PAGE under reducing conditions. The protein was purified on a Cobalt affinity column in a buffer containing 8M urea. The urea was removed by dialysis against 50 mM Tris-HCL, pH 8.0, and 100 mM Na Cl.

N-terminal Assay

Cell lysates were thawed and diluted 1:16 in diluent buffer (1×PBS, 5% BSA, 0.12% SDS, 0.01% NP-40, pH 7.0). Fifty microliters of sample was added to streptavidan plates followed by 50 µl biotin labeled Mab BR1N411.4 at 4 µg/ml. Plates were incubated for 3 hours with shaking. Plates were washed with 1×PBS/0.1% Tween 20. One hundred microliters of Europium labeled Mab BR1N129.5 at 2 µg/ml was added to each well for a 1 hour incubation with shaking. Plates were washed, rinsed with water, and blotted dry. 120 µl of Wallac Enhancement Solution was added to each well for 5 minutes. Plates were read on a Delfia reader.

Full-Length Assay

The same format was used as described for the N-terminal assay with the following changes: biotin labeled BR1S425.1 at 4 µg/ml was added to the sample and incubated for 1 hour with shaking. Europium labeled BR1N129.5 was added at a concentration of 4 µg/ml.

Results

Lysates were prepared from each of the human lymphoblastoid cell lines (HLC) as described in the methods section. The cell lines and known mutations are detailed in Table 1.

was used to generate statistics comparing normal HLC to the BRCA1 mutant HLC. The results are shown in Tables 2 and 3, and shown in FIGS. 1 and 2. In both assays, the normal lysates had higher levels of BRCA1 protein than in the BRCA1 mutated cell line. This difference is statistically significant. ($p=0.001$).

TABLE 2

Quantitation of BRCA1 proteins in HLC lysates: "Lot 1"

| Cell Line | Mutation | mean RFU N assay[a] | cal. value N assay[b] | mean RFU FL assay[c] | cal. value FL assay[d] |
|---|---|---|---|---|---|
| HS53089 | none | 659261.36 | 735.51 | 217808.00 | 31.16 |
| MB61490 | none | 663546.72 | 740.30 | 341306.64 | 48.77 |
| CG71291 | none | 688421.36 | 768.07 | 263810.72 | 37.72 |
| SFM03592 | none | 759760.00 | 847.72 | 324984.00 | 46.44 |
| GM13706A | Cys64Gly | 78578.64 | 87.21 | 117052.00 | 16.78 |
| GM13710 | Arg1443Gly | 108642.64 | 120.78 | 127229.36 | 18.24 |
| GM13711 | S1040N | 86354.64 | 95.90 | 103657.36 | 14.87 |
| GM14092 | Val1713Ala | 96098.72 | 106.77 | 137420.00 | 19.69 |
| GM14097 | Cys61Gly | 96952.00 | 107.73 | 124061.28 | 17.78 |
| 96–101 | 185delAG | 88576.00 | 98.38 | 101997.36 | 14.64 |
| 97–122 | 1293del40 | 99109.98 | 110.14 | 84030.64 | 12.07 |
| GM13707 | 1294del40 | 288656.00 | 321.75 | 173713.36 | 24.87 |
| GM13708 | Glu1564ter | 239960.00 | 267.39 | 136698.72 | 19.59 |

TABLE 1

Human Lymphoblastoid Cell Lines

| Cell Line | Mutation | Cell Line | Mutation | Cell Line | Mutation | Cell Line | Mutation | Cell Line | Mutation |
|---|---|---|---|---|---|---|---|---|---|
| HS53089 | none | GM13706A | Cys64Gly | 96–101 | 185delAG | 97–124 | 3875del4 | GM13714A | 5438insC |
| MB61490 | none | GM13710 | Arg1443Gly | 97–122 | 1293del40 | GM13705 | 3975del4 | GM13715 | 5382insC |
| CG71291 | none | GM13711 | S1040N | GM13707 | 1294del40 | GM13709 | 2135delA | GM14091 | 5382insC |
| SFM03592 | none | GM14092 | Val1713Ala | GM13708 | Glu1564ter | GM13712 | 2279insA | GM14095 | 5256delG |
|  |  | GM14097 | Cys61Gly | GM13713 | Gly1250ter | GM14096 | 3600del11 | 97–120 | 5382insC |
|  |  |  |  | GM14090 | 185delAG |  |  | 97–121 | 5382insC |
|  |  |  |  | GM14093 | 1323delG |  |  |  |  |
|  |  |  |  | GM14094 | 1294del40 |  |  |  |  |

This table lists the cell line name and the BRCA1 mutation of the cell line for the human lymphoblastoid cell lines used in this study. Cell lines are grouped based on a similar mutational status, i.e. the first set of cell lines contain no BRCA1 mutations, while the second set are cell lines with base substitutions in the BRCA1 gene. The third, fourth and fifth set of cell lines yield truncated BRCA1 protein of varying length from short segments, under 300 amino acids, mid-length fragments of 300–1300 amino acids and long segments of greater than 1300 amino acids.

Fusion Calibrator Assay Results

The performance of the fusion calibrator in the N-terminal and full-length assays was determined. In both assays, the calibrator is linear upon dilution. Results are shown in mean Relative Fluorescent Units (RFU). The calibrator range was between 1 and 200 nag/ml.

Figure 2:
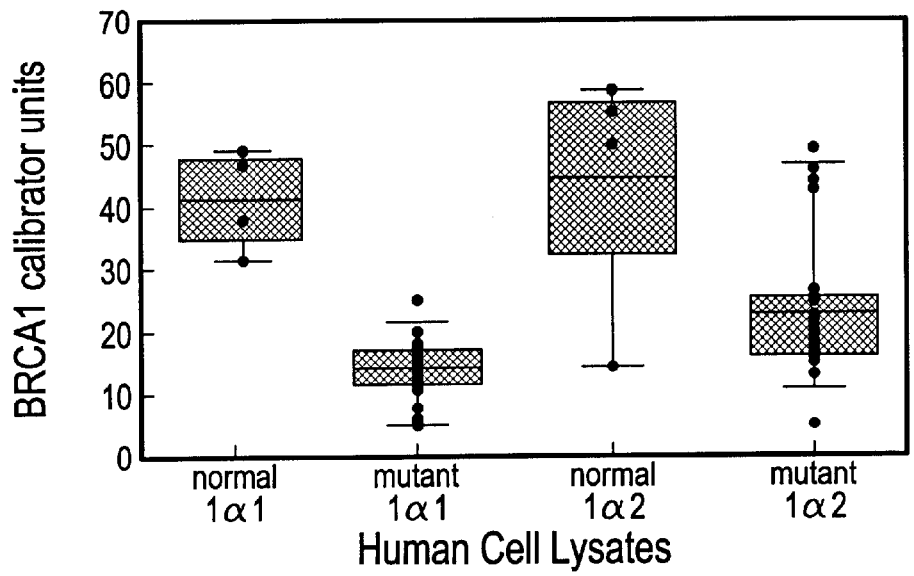
FIG. 2 is a diagram that shows the statistical comparison of Normal and BRCA1 mutant HLC in the full-length assay.

FIG. 1 graphs the performance of the fusion calibrator in the N-terminal and full-length assays. In both assays, the calibrator is linear upon dilution. Results are shown in mean Relative Fluorescent Units (RFU). The calibrator range was between 1 and 200 ng/ml.

Quantitation of BRCA1 Polypeptides in HLC Lysates

Lysates were thawed and diluted 1:16 in the appropriate assay buffer. Each lysate lot was run in triplicate. Results are shown in Tables 2 and 3. The mean RFU for each lysate was converted into BRCA1 ng/ml equivalent calibrator units (cal values in Tables 2 and 3) based on the linear equation generated by the fusion protein calibrator. These cal values were used since each different BRCA1 polypeptide can have a different molecular weight and therefore require a unique standard. This one standard is a simple convenient means to assess the assay response on a common basis. A simple T test TABLE 2-continued Quantitation of BRCA1 proteins in HLC lysates: "Lot 1"

| Cell Line | Mutation | mean RFU N assay[a] | cal. value N assay[b] | mean RFU FL assay[c] | cal. value FL assay[d] |
|---|---|---|---|---|---|
| GM13713 | Glu1250ter | 60911.32 | 67.49 | 115149.28 | 16.51 |
| GM14090 | 185delAG | 83666.72 | 92.89 | 111482.64 | 15.99 |
| GM14093 | 1323delG | 50357.36 | 55.71 | 119690.64 | 17.16 |
| GM14094 | 1294del40 | 49805.32 | 55.09 | 100513.36 | 14.42 |
| 97–124 | 3875del4 | 9484.00 | 10.07 | 30848.00 | 4.49 |
| GM13705 | 3875del4 | 20437.36 | 22.30 | 34917.36 | 5.07 |
| GM13709 | 2135delA | 19080.00 | 20.79 | 40374.64 | 5.85 |
| GM13712 | 2279insA | 49725.36 | 55.00 | 95224.00 | 13.67 |
| GM14096 | 3600del11 | 56381.36 | 62.43 | 123725.36 | 17.74 |
| GM13714A | 5438insC | 105592.00 | 117.37 | 111524.00 | 16.00 |
| GM13715 | 5382insC | 103672.00 | 115.23 | 73448.00 | 10.56 |
| GM14091 | 5382insC | 74019.34 | 82.12 | 117818.64 | 16.89 |
| GM14095 | 5256delG | 120732.45 | 134.28 | 113866.64 | 16.33 |

TABLE 2-continued

Quantitation of BRCA1 proteins in HLC lysates: "Lot 1"

| Cell Line | Mutation | mean RFU N assay[a] | cal. value N assay[b] | mean RFU FL assay[c] | cal. value FL assay[d] |
|---|---|---|---|---|---|
| 97–120 | 5382insC | 13822.64 | 14.92 | 32736.00 | 4.76 |
| 97–121 | 5382insC | 41048.00 | 45.31 | 52645.28 | 7.60 |

[a]N-terminal assay results in mean Relative Fluorescent Units (RFU) of triplicate wells.
[b]BRCA1 calibrator units for the N-terminal assay were calculated using the following equation, as determined by the calibrator performance: y = 460.69 + 895x, where y = mean RFU and x = the calculated value.
[c]The mean RFU of triplicate wells in the full-length assay.
[d]The mean RFU in the full-length assay was converted into BRCA1 calibrator units using the following equation determined by the calibrator performance: y = 609.26 + 7010.39x, where y = mean RFU and x = the calculated value.

TABLE 3

Quantitation of BRCA1 proteins in HLC lysates: "Lot 2"

| Cell Line | Mutation | mean RFU N assay[a] | cal. value N assay[b] | mean RFU FL assay[c] | cal. value FL assay[d] |
|---|---|---|---|---|---|
| HS53089 | none | 102821.36 | 114.28 | 96040.00 | 13.79 |
| MB61490 | none | 668229.28 | 745.53 | 407456.00 | 58.21 |
| CG71291 | none | 851218.72 | 949.82 | 345256.00 | 49.34 |
| SFM03592 | none | 781570.72 | 872.07 | 383912.00 | 54.85 |
| GM13706A | Cys64Gly | 14426.64 | 15.59 | 28168.00 | 4.10 |
| GM13710 | Arg1443Gly | 90192.00 | 100.18 | 102637.36 | 14.73 |
| GM13711 | S1040N | 173220.00 | 192.88 | 150188.00 | 21.51 |
| GM14092 | Val1713Ala | 64760.00 | 71.79 | 106158.64 | 15.23 |
| GM14097 | Cys61Gly | 83328.00 | 92.52 | 125456.00 | 17.98 |
| 96–101 | 185delAG | 95458.64 | 106.06 | 116841.36 | 16.75 |
| 97–122 | 1293del40 | 88482.30 | 98.27 | 85364.61 | 12.26 |
| GM13707 | 1294del40 | 771581.28 | 860.91 | 291853.36 | 41.72 |
| GM13708 | Glu1564ter | 793653.36 | 885.56 | 336901.36 | 48.14 |
| GM13713 | Glu1250ter | 100944.00 | 112.18 | 130701.36 | 18.73 |
| GM14090 | 185delAG | 253917.28 | 271.81 | 179442.64 | 25.68 |
| GM14093 | 1323delG | 101677.28 | 113.00 | 136920.00 | 19.62 |
| GM14094 | 1294del40 | 79760.00 | 88.53 | 98266.64 | 14.10 |
| 97–124 | 3875del4 | 402986.64 | 449.40 | 155325.36 | 22.24 |
| GM13705 | 3875del4 | 602512.00 | 672.16 | 301850.64 | 43.14 |
| GM13709 | 2135delA | 51757.28 | 57.27 | 102312.00 | 14.68 |
| GM13712 | 2279insA | 708893.28 | 790.93 | 167128.00 | 23.93 |
| GM14096 | 3600del11 | 51245.32 | 56.70 | 107221.36 | 15.38 |
| GM13714A | 5438insC | 756813.28 | 844.43 | 313797.36 | 44.85 |
| GM13715 | 5382insC | 103672.00 | 115.23 | 73448.00 | 10.56 |
| GM14091 | 5382insC | 107117.28 | 119.08 | 177157.36 | 25.36 |
| GM14095 | 5256delG | 96346.72 | 107.05 | 145800.00 | 20.88 |
| 97–120 | 5382insC | 65303.34 | 72.39 | 111053.36 | 15.93 |
| 97–121 | 5382insC | 80776.02 | 89.67 | 84554.72 | 12.15 |

[a]N-terminal assay results in mean Relative Fluorescent Units (RFU) of triplicate wells.
[b]BRCA1 calibrator units for the N-terminal assay were calculated using the following equation, as determined by the calibrator performance: y = 460.69 + 895x, where y = mean RFU and x = the calculated value.
[c]The mean RFU of triplicate wells in the full-length assay.
[d]The mean RFU in the full-length assay was converted into BRCA1 calibrator units using the following equation determined by the calibrator performance: y = 609.26 + 7010.39x, where y = mean RFU and x = the calculated value.

Deposit Information

A deposit of the monoclonal antibodies BR1N129.5, BR1N411.4, BR1H945.2, BR1H826.5, BR1H788.6, BR1S425.1, BR1S060.2, BR1S218.1, and BR1S384.5 disclosed above and recited in the appended claims has been made with the American Type Culture Collection (ATCC), 10801 University Boulevard, Manassas, Va. 20110.

The date of deposit was May 8, 2002. The ATCC accession numbers have been assigned as follows:

Mouse hybridoma line BR1H-788.6 was assigned PTA-4301.

Mouse hybridoma line BR1H-826.5 was assigned PTA-4302.

Mouse hybridoma line BR1H-945.2 was assigned PTA-4303.

Mouse hybridoma line BR1N-129.5 was assigned PTA-4304.

Mouse hybridoma line BR1N-411.4 was assigned PTA-4305.

Mouse hybridoma line BR1S-060.2 was assigned PTA-4306.

Mouse hybridoma line BR1S-218.1 was assigned PTA-4307.

Mouse hybridoma line BR1S-384.5 was assigned PTA-4308.

Mouse hybridoma line BR1S-425.1 was assigned PTA-4309.

The deposit will be maintained in the depository for a period of 30 years, or 5 years after the last request, or for the effective life of the patent, whichever is longer, and will be replaced as necessary during that period.

REFERENCE LIST

1. Futreal, P. A., Shattuck-Eidens, D., Liu, Q., Cochran, C., and Harshman, K. 1994. BRCA1 mutations in primary breast and ovarian carcinomas, *Science*, 266: 120–122.
2. Castilla, L. H., Couch, F. J., Erdos, M. R., Hoskins, K. F., Calzone, K., Garber, J. E., Boyd, J., Lubin, M. B., DeShano, M. L., Brody, L. C., Collins, F. S., and Weber, B. L. 1994. *Nature Genet.*, 8:387–391.
3. Plummer, S. J. 1995. Detection of BRCA1 mutations by the protein truncation test, *Human Molecular Genetics*, 4: 1989–1991.
4. Gao, M. and Knipe, D. M. 1992. Distal protein sequences can affect the function of a nuclear localization signal, *Mol. Cell. Biol.*, 12: 1330–1339.
5. Dawson, J. M. 1999. Clinical Trials: Analysis and Presentation, Presented at the 26th Annual Meeting of the Association of Medical Diagnostics Manufacturers, Available at http://www.amdm.org/AMDM/NewsletterV12-2-2.html
6. Linnet, K. 1999. Necessary sample size for method comparison studies based on regression analysis. *Clin. Chem.*, 45: 882–94.
7. Linnet, K. 1993. Evaluation of regression procedures for methods comparison studies. *Clin. Chem.*, 39: 424–32.
8. Bland, J. M., Altman, D. G. 1986. Statistical methods for assessing agreement between two methods of clinical measurement. *Lancet*, i: 307–10.
9. Reid, M. C., Lachs, M. S., Feinstein A. R. 1995. Use of methodologic standards in diagnostic test research. Getting better but still not good. *JAMA*, 274: 645–51.
10. Krouwer, J. S. Cumulative distribution analysis graphs—an alternative to ROC curves [Tech Brief]. *Clin. Chem.*, 33: 2305–6.
11. Albert, A. 1982. On the use and computation of likelihood ratios in clinical chemistry. *Clin. Chem.*, 28: 1113–9.
12. Solberg, H. E. 1978. Discriminant analysis. *Crit. Rev. Clin. Lab. Sci.*, 9: 209–42.
13. Matthews, J. N. S., Altman, D. G., Campbell, M. J., Royston, P. 1990. Analysis of serial measurements in medical research. *Br. Med. J.*, 300: 230–5.
14. Kohler, G. and Milstein, C., "Continuous cultures of fused cells secreting antibody of predefined specificity," *Nature*, 256: 495–497, 1975.

15. Kuus-Reichel, K., Knott, C., Liu, R., and Wolfert, R. L., "Development of antibodies for diagnostic assays," C. P. Price and D. J. Newman (eds.), Principles and Practice of Immunoassay, pp. 37–64, New York: Stockton Press. 1997.

What is claimed is:

1. A method for detecting and determining the presence of a mutation in the BRCA1 gene of a subject comprising the steps of:

(a) determining the amount of BRCA1 polypeptide contained in a sample of the subject by using an antibody selected from the group consisting of BR1N129.5, BR1N411.4, BR1H945.2, BR1H826.5, BR1H788.6, BR1S060.2, BR1S218.1, BR1S425.1, and BR1S384.5., and (b) correlating the amount of BRCA1 to the presence of the BRCA1 gene mutation in the subject, wherein the amount below a pre-determined cutoff value is an indication of the presence of the mutation in the BRCA1 gene of the subject.

2. The method of claim 1, wherein the sample is a biological fluid sample selected from the group consisting of peripheral blood lymphocyte (PBL) lysates, tissue lysates, cells lysates, and serum samples.

3. The method of claim 2, wherein the sample is cell lysates.

4. The method of claim 1, wherein step (a) further comprises the steps of:

(a) contacting said antibody with the sample under a condition that allows the formation of a complex comprising the antibody and the BRCA1 polypeptide;

(b) detecting and determining the amount of complex.

5. The method of claim 4, wherein the antibody comprises a detectable label or is capable of binding to a detectable label for forming a detectable complex.

6. The method of claim 4, wherein the sample is a biological fluid sample, and wherein said antibody is attached to a solid phase.

7. The method of claim 6, wherein the complex is detected by a second antibody which comprises a detectable label or which is capable of binding to a detectable label for forming a detectable complex.

8. The method of claim 7, wherein said second antibody is a monoclonal antibody.

9. The method of claim 8, wherein one of the monoclonal antibodies recognizes one end region of the BRCA1 polypeptide, and another monoclonal antibody recognizes a portion of the BRCA1 polypeptide that is sufficiently remote from the end region of the BRCA1 polypeptide to allow the binding of both monoclonal antibodies to the BRCA1 polypeptide.

10. The method of claim 8, wherein one of the monoclonal antibodies is immunoreactive with the N-terminal of the BRCA1 polypeptide and another monoclonal antibody is immunoreactive with the C-terminal of the BRCA1 polypeptide.

11. The method of claim 8, wherein one of the monoclonal antibodies is immunoreactive with the N-terminal of the BRCA1 polypeptide and another monoclonal antibody is immunoreactive with a portion of the BRCA1 polypeptide.

12. The method of claim 8, wherein one of the monoclonal antibodies is immunoreactive with the C-terminal of the BRCA1 polypeptide and another monoclonal antibody is immunoreactive with a portion of the BRCA1 polypeptide.

13. The method of claim 1, wherein the mutation is an insertion, deletion or base substitution.

14. The method of claim 1, wherein the mutation is a germline mutation or a somatic mutation.

* * * * *

UNITED STATES PATENT AND TRADEMARK OFFICE
CERTIFICATE OF CORRECTION

PATENT NO. : 6,514,713 B1
DATED : February 4, 2003
INVENTOR(S) : Knott et al.

Page 1 of 1

It is certified that error appears in the above-identified patent and that said Letters Patent is hereby corrected as shown below:

Delete Column 13, lines 52-56,

"FIG. 1 graphs the performance of the fusion calibrator in the N-terminal and full-length assays. In both assays, the calibrator is linear upon dilution. Results are shown in mean Relative Fluorescent Units (RFU). The calibrator range was between 1 and 200 ng/ml."

Signed and Sealed this

Twenty-third Day of March, 2004

JON W. DUDAS
*Acting Director of the United States Patent and Trademark Office*